United States Patent [19]
Hartwig

[11] Patent Number: 5,993,377
[45] Date of Patent: Nov. 30, 1999

[54] ANAL BEADS

[76] Inventor: Lee Ann Hartwig, 320 W. Branch Ave., Hidden Valley G, Pine Hill, N.J. 08021

[21] Appl. No.: 09/012,421

[22] Filed: Jan. 23, 1998

[51] Int. Cl.$^6$ ...................................................... A61F 5/00
[52] U.S. Cl. .............................................................. 600/38
[58] Field of Search .......................... 600/38–41; 607/96, 607/104, 105, 113, 114

[56] References Cited

U.S. PATENT DOCUMENTS

| | | | |
|---|---|---|---|
| 3,726,273 | 4/1973 | Cole | ...................................... 600/38 X |
| 3,939,842 | 2/1976 | Harris . | |
| 4,841,970 | 6/1989 | Rand . | |
| 4,938,221 | 7/1990 | Tuffel . | |
| 5,387,179 | 2/1995 | Crivellaro | .................................. 600/38 |
| 5,470,625 | 11/1995 | Perrault | ................................. 607/114 X |

*Primary Examiner*—Samuel Gilbert
*Attorney, Agent, or Firm*—Norman E. Lehrer

[57] ABSTRACT

A sexual aid in the form of a string of anal beads is provided wherein each bead is preferably in the form of a hollow spherical plastic shell. A liquid or gel fills the hollow spheres of the beads and can be heated or chilled prior to use. The liquid or gel is chosen so as to be able to retain the cold or heated temperature for a substantial period of time whereby the beads can transfer the heat or cold to the human body over a period of time during the use of the anal beads.

9 Claims, 1 Drawing Sheet

ANAL BEADS

BACKGROUND OF THE INVENTION

The present invention is directed toward a sexual aid for increasing the sexual pleasure of both men and women during orgasm and more particularly toward a sexual aid in the form of anal beads wherein each bead contains a liquid or gel that can be prechilled or preheated prior to use.

Anal beads, per se, have been known and used for many centuries as a sex aid to increase sexual pleasure. While no one, of course, knows for certainty, the common belief is that such devices originated with the ancient Chinese.

Conventional anal beads are essentially a string of beads. Each bead is generally spherical in shape having a diameter of between one quarter inch and three quarters of an inch. From three to six or seven or more beads are carried on the string and are normally spaced from each other the distance of approximately one to two inches. The free end of the string has a handle portion preferably in the form of a loop or finger ring or the like.

Conventional anal beads are used by first inserting all the beads into the rectal canal passed the sphincter muscle leaving only the loop or finger ring exposed. A lubricant such as KY jelly or the like may be utilized with the beads in order to aid in the insertion process. During sexual activity and particularly when experiencing orgasm, the beads are removed by pulling on the finger ring. This can be done relatively quickly or slowly depending on the desires of the person utilizing the same. Different people will, of course, have different reactions and responses to the sensations experienced through the use of such device.

Through the years, anal beads have been made from various materials including glass or ceramics, metals, plastics and numerous others. To Applicant's knowledge, however, there have essentially been no changes or improvements to anal beads since the beginning of their use. Applicant has found that increased pleasure can be obtained by first chilling or heating the beads before use and, to this end, has designed anal beads which have a fluid reservoir within each bead that can be chilled or heated and which will retain its heated or cooled temperature for a substantially period of time.

While devices having a fluid reservoir therein for heating or cooling the rectal area have previously been known, these have been therapeutic devices for treating hemorrhoids and other inflammations. Such devices are described, for example, in U.S. Pat. Nos. 3,939,842; 4,841,970 and 4,938,221. To Applicant's knowledge, however, no one has proposed to utilize cooled or heated materials rectally in order to increase sexual pleasure.

SUMMARY OF THE INVENTION

The present invention is designed to overcome the deficiencies of the prior art discussed above. It is an object of the present invention to provide anal beads which are designed to increase sexual pleasure beyond the use of conventional anal beads.

It is a further object of the invention to provide anal beads which include a fluid reservoir within each bead for containing a liquid or gel like substance.

It is even a further object of the invention to provide anal beads having a liquid or gel-like material within each bead which can be either heated or cooled prior to use.

In accordance with the illustrated embodiments, demonstrating features and advantages of the present invention, there is provided a string of anal beads wherein each bead is preferably comprised of a hollow spherical plastic. A liquid or gel fills the hollow spheres of the beads and can be heated or chilled prior to use. The liquid or gel is chosen so as to be able to retain the cold or heated temperature for a substantial period of time whereby the beads can transfer the heat or cold to the human body over a period of time during the use of the anal beads.

BRIEF DESCRIPTION OF THE DRAWINGS

For the purposes of illustrating the invention, there is shown in the accompanying drawings one form which is presently preferred; it being understood that the invention is not intended to be limited to the precise arrangements and instrumentalities shown.

DETAILED DESCRIPTION OF THE PREFERRED EMBODIMENT

Figure 1:
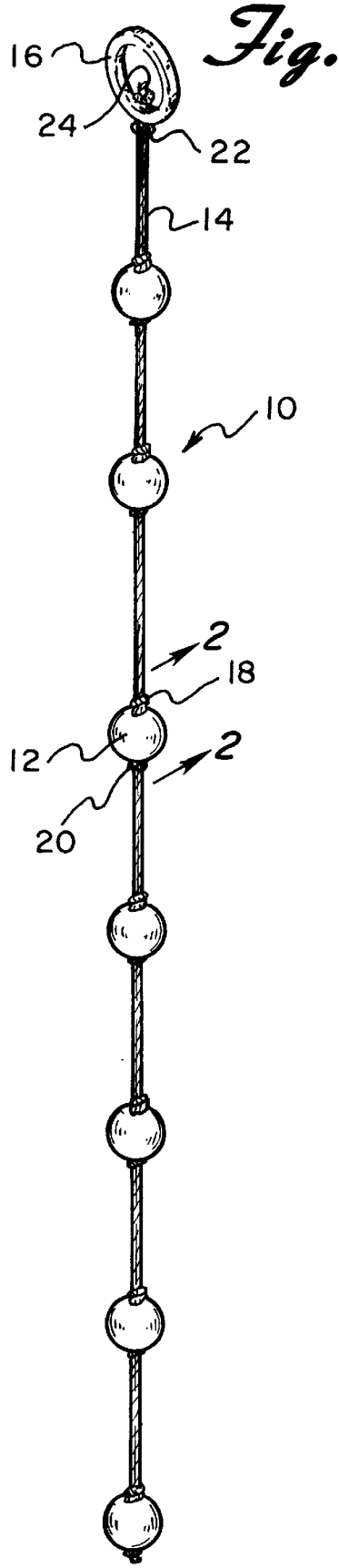
FIG. 1 with a perspective view of anal beads in accordance with the present invention.

Referring now to the drawings in detail where in like reference numerals have been used in the two figures to designate like elements, there is shown in FIG. 1 a perspective view of anal beads constructed in accordance with the principles of the present invention and designated generally as 10. The anal beads 10 of the invention are comprised essentially of a plurality of beads 12, an elongated flexible string 14 and a loop or finger ring 16 at the upper free end thereof. The beads 12 are preferably spherically shaped although other smooth, rounded shapes may also be possible. In the illustrated embodiment, seven beads are shown. It should be understood, however, that this is by way of example only and that a fewer or greater number of beads could be utilized.

As is known in the art, the beads are connected to the string 14 by passing the string through an opening formed through the interior thereof. The details of this will be described in more detail hereinafter with respect to the present invention when reference is made to FIG. 2.

A knot such as shown at 18 is formed at the top of each of the beads and a similar knot such as shown at 20 is formed at the bottom. Obviously other types of small claps or devices could be used in order to prevent each bead from sliding along the length of the string 14. For example, if the beads and/or string 14 where made of a thermoplastic material, the beads could be heat bonded to the string to prevent movement there along. Epoxies or other types of adhesive materials could also be utilized.

Each bead is preferably between one quarter inch and three quarters inch in diameter. This may, of course, vary depending on the shape of the bead and individual preferences. The beads may be spaced apart from each other by approximately one inch to two inches. Again, however, this spacing may vary depending on personal preferences. The string 14 may be made of any number of materials from natural cotton to artificial fibers such as nylon or the like. The only requirements being, however, that the string 14 be very flexible and relatively strong. The string 14 along with the remaining parts of the anal beads must, of course, also be capable of being cleaned and disinfected without having any detrimental effect on the same.

The loop or finger ring 16 secured to the top end 22 of the string 14 may also be made of plastic or metal or substantially any other material. The finger ring 16 may be attached to the string 14 by tying the end 12 around the ring or, as in the embodiment shown, the end 22 of the string 14 may pass through a small opening in the side wall of the ring 16 and may be secured thereto by tying a knot 24 in the end 22 of the string 14.

Figure 2:
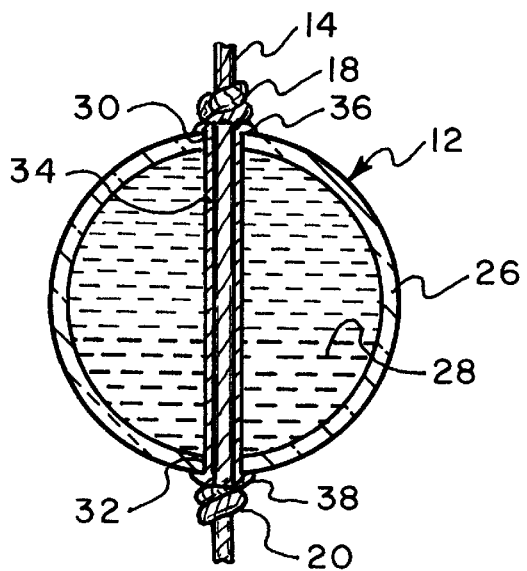
FIG. 2 is a cross sectional view taken through the line 2—2 of FIG. 1.

The details of each of the beads 12 are shown most clearly in FIG. 2. While only one bead 12 is being described with reference to FIG. 2, it should be understood that each of the beads shown in FIG. 1 is constructed in essentially the same manner. A detailed description of each of the beads is, therefore, not believed to be necessary.

Each bead 12 is comprised of a plastic spherical shell 26 which defines an essentially spherical cavity therein. This cavity if filled with a congealable liquid such as water, ethylene glycol, propylene glycol or any number of other liquids or gels which are capable of being chilled or frozen and which will tend to retain the frozen state or chilled temperature. Similarly, such liquids or gels or other types of materials could be used which, when heated, tend to maintain their heated temperature. In each case, however, the temperature of the liquid or gel 28 within the shell 26 of the bead 12 will be able to transfer the cold or heat through the wall of the shell 26 to the human body. Any number of plastics or other materials could be used for the shell 26 although it is believed that polyethylene or some other material which is nonreactive to body tissues is most desirable.

As pointed out above, the string 14 passes through the center of each of the beads 12. In order to accomplish this, the bead has an opening 30 at the top thereof and a similar opening 32 directly opposite at the bottom of the bead. However, in order to prevent the liquid or gel 28 from spilling out of the interior of the bead 12 through one of the openings 30 or 32, a tubular member 34 passes through the interior of the bead 12 and is sealed at its top and bottom as shown at 36 and 38. In this way, the string 14 actually passes through the center of the tube 34 and never comes into contact with the liquid or gel 28.

The present invention may be embodied in other specific forms without departing from the spirit or essential attributes thereof and accordingly, reference should be made to the appended claims rather than to the foregoing specification as indicating the scope of the invention.

I claim:

1. A sexual aid comprising:

an elongated flexible string;

a plurality of round elements, each of said elements being comprised of a hollow shell of plastic material capable of containing a liquid therein without the same leaking to the exterior thereof, each of said elements being mounted on said string and being spaced apart from each other, and a congealable liquid contained within each of said elements.

2. The sexual aid as claimed in claim 1 wherein at least some of said elements are spherically shaped.

3. The sexual aid as claimed in claim 1 wherein said round elements are in the form of substantially hollow beads.

4. The sexual aid as claimed in claim 3 wherein said string passes through the center of each of said beads.

5. The sexual aid as claimed in claim 3 wherein said beads have a diameter of between approximately one quarter inch to approximately three quarters of an inch.

6. The sexual aid as claimed in claim 5, wherein said beads are spaced apart from each other along said string by a distance of between approximately one to two inches.

7. The sexual aid as claimed in claim 6, wherein there are at least three beads.

8. The sexual aid as claimed in claim 1 further including a handle member secured to one end of said string.

9. The sexual aid as claimed in claim 8, wherein said handle member is in the form of a loop.

* * * * *